Feb. 20, 1962 E. H. DOERR Plant Pat. 2,131
GLADIOLUS PLANT
Filed Jan. 13, 1961
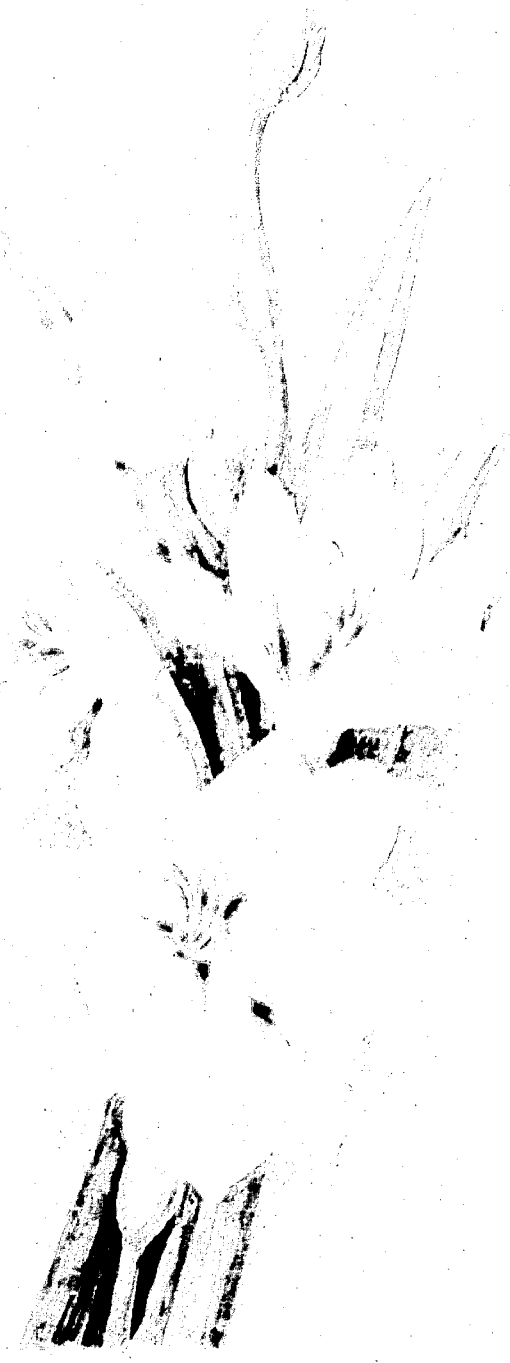
WITNESS
Addison E. Avery
INVENTOR
ERVIN H. DOERR
by Rummler & Lucas
ATTYS.

United States Patent Office

Plant Pat. 2,131
Patented Feb. 20, 1962

2,131
GLADIOLUS PLANT

Ervin H. Doerr, 1516 N. Broadway, New Ulm, Minn.

Filed Jan. 13, 1961, Ser. No. 82,663
1 Claim. (Cl. 47—60)

This invention relates to gladiolus plants and particularly to a new and distinct variety of multiple or double gladiolus characterized by the novel pink color of its blooms and the fact that the flowers are fragrant.

This new variety of gladiolus plant was discovered by me in my nurseries at New Ulm, Minnesota, and is the result of breeding efforts carried on by me for more than twenty years with the object of creating improvements in double gladiolus varieties and particularly to develop a double gladiolus having a pleasing fragrance.

My new discovery originated as a seedling of "Beauty Blush" (unpatented), as the seed parent, and "Multi Petal" (unpatented), as the pollen parent, and has been asexually reproduced by me from cormels at New Ulm, Minnesota. Asexual reproduction of this new variety through successive generations has shown its distinctive features to hold true to form and to be fixed.

The new plant structure of my new variety of gladiolus plant is substantially the same as that of the gladiolus family, the plant growing vigorously to a height of about 30 inches with abundant sword shaped leaves and medium sized double flowers growing singly on sturdy spikes borne by upright stems. The plant blooms once and profusely, in midseason or summer, the flowers having an opened diameter of approximately 3 inches. The flowers have a good lasting quality both on the plant and as cut flowers and the petals stay on the stems until the plant has bloomed out.

The new variety is particularly distinguished in that the blooms are of a beautiful pink color, with a rather frilly appearance due to crinkling and curling of the petal margins, particularly adjacent the tips, and have a very definite fragrance of the odor of honey. To the best of my knowledge this new variety is the first fragrant double-flower gladiolus plant and I know of no variety that it closely resembles.

My new variety of gladiolus plant is illustrated by the accompanying full color drawing which shows a cluster of the blooms and includes partly opened buds as well as foliage.

The following is a more detailed description of my new gladiolus variety:

*Plant*

Form: Conventional gladiolus.
Height: Approximately 30 inches.
Growth: Vigorous and upright.
Foliage: Abundant sword shaped leaves of conventional form and color. Glossy texture.

*Bud*

Form: Ovoid.
Color:
*Sepals.*—Green.
*Petals.*—When sepals first divide—pale green, tipped with pink as petals begin to unfurl.

*Flower*

Blooms: Once, in midseason of summer, with profuse production of flowers.
Size: Medium, approximately 3 inches in diameter.
Borne: Singly, on closely spaced stems.
Shape: Substantially same as usual gladiolus but with marginally crinkled or curled petals. Form does not change as flower ages.
Petalage: 6 to 10 petals.
*Color.*—Outer petals—dull pink. Inside petals—light pink.
*Persistence.*—Petals stay on stem until plant is bloomed out. Flowers hang on and dry.
*Texture.*—Soft.
*Appearance.*—Velvety.
Fragrance: Odor of honey.
Lasting quality: Good, on plant and as cut flower. Blooms are not affected by wet or hot weather.

*Genital organs*

Stamens: Anthers, three in number.
Pollen: Gray in color.
Pistils: One—about 1 inch long.
Ovaries: Normal.

The color designations for this new variety of gladiolus plant, according to Maerz and Paul Dictionary of Color, are as follows:

| | Plate | Letter | Number |
|---|---|---|---|
| Full Flower: | | | |
| Inside or front side of Petals— | | | |
| from | 1 | A | 2 |
| through | 1 | B | 2 |
| and | 1 | C | 2 |
| to edges and tips of Petals | 1 | D | 2 |
| and | 1 | E | 2 |
| marking outward from center of base | 54 | L | 12 |
| Back side of Petals | 1 | G | 3 |
| Pistil and Stamens, generally white (some reddish) some tipped with | 43 | C | 4 |
| Buds: | | | |
| Sepals, green | 18 | L | 7 |
| Petals, when beginning to unfurl | 10 | J | 1 |
| tipped with dull pink | 4 | A | 3 |
| Foliage: | | | |
| green | 18 | L | 7 |
| to | 18 | L | 8 |

As before indicated, the outstanding and distinctive characteristics of my new gladiolus plant are the attractive pink color of the double flowers and the honey-like fragrance of the blooms, which features are believed to be wholly new in the multiple or double type of gladiolus and serve to make the new variety specially attractive as a decorative type useful for floral arrangements.

Having thus described my new variety of gladiolus plant, I claim:

A new and distinct variety of gladiolus plant, substantially as herein shown and described, characterized particularly by the soft and pale pink color of its medium sized double flowers and by the distinct honey-like fragrance of the flowers in bloom.

No references cited.